(12) United States Patent
Laflamme et al.

(10) Patent No.: US 7,547,450 B2
(45) Date of Patent: Jun. 16, 2009

(54) SENIOR FELINE FOOD

(75) Inventors: Dorothy P Laflamme, Millstadt, IL (US); Barbara McCracken, Birmingham, AL (US)

(73) Assignee: Nestec Ltd., Vevey (CH)

( * ) Notice: Subject to any disclaimer, the term of this patent is extended or adjusted under 35 U.S.C. 154(b) by 698 days.

(21) Appl. No.: 10/065,499

(22) Filed: Oct. 24, 2002

(65) Prior Publication Data

US 2004/0081743 A1   Apr. 29, 2004

(51) Int. Cl.
*A23K 1/16* (2006.01)
(52) U.S. Cl. .................. 424/442; 514/562; 514/564; 426/805
(58) Field of Classification Search .................. 424/442
See application file for complete search history.

(56) References Cited

U.S. PATENT DOCUMENTS

| | | | |
|---|---|---|---|
| 4,000,318 A | 12/1976 | Ferguson et al. | |
| 4,267,195 A * | 5/1981 | Boudreau et al. | 426/2 |
| 4,735,808 A | 4/1988 | Scaglione et al. | |
| 5,792,401 A | 11/1998 | Lepine | |
| 5,882,714 A | 3/1999 | Lepine | |
| 5,997,915 A | 12/1999 | Bailey et al. | |
| 6,039,952 A | 3/2000 | Sunvold et al. | |
| 6,106,870 A | 8/2000 | Rohrberg et al. | |
| 6,132,724 A | 10/2000 | Blum | |
| 6,159,942 A | 12/2000 | St. Cyr et al. | |
| 6,203,820 B1 * | 3/2001 | Vickery | 424/646 |
| 6,245,379 B1 * | 6/2001 | Lepine | 426/656 |
| 6,306,442 B1 | 10/2001 | Sunvold et al. | |
| 6,310,090 B1 | 10/2001 | Hayek | |
| 6,429,198 B1 | 8/2002 | St. Cyr et al. | |
| 6,479,069 B1 | 11/2002 | Hamilton | |
| 6,488,970 B1 | 12/2002 | Hora | |
| 2001/0043983 A1 | 11/2001 | Hamilton | |
| 2002/0072501 A1 | 6/2002 | St. Cyr et al. | |
| 2002/0119237 A1 | 8/2002 | Hevey | |
| 2002/0178079 A1 | 11/2002 | Russell et al. | |
| 2003/0009370 A1 | 1/2003 | Singh et al. | |

FOREIGN PATENT DOCUMENTS

| | | |
|---|---|---|
| EP | 0 609 056 | 12/1999 |
| GB | 2130071 | * 5/1984 |

OTHER PUBLICATIONS

Labdiet—Ferret Diet 5280—Aug. 1998.*
Merck Veterinary Manual pp. 1354,1355 1967.*
Iams : A Cat Food Cats Fancy, for Some Catss, Less is More, The Puurfect Compement—Oct. 1993.*

* cited by examiner

*Primary Examiner*—Neil Levy
(74) *Attorney, Agent, or Firm*—K&L Gates LLP

(57) ABSTRACT

A feline pet food comprising a dietary level of protein and a supplemental amount of at least one amino acid in an amount sufficient to provide a feline lean body mass protection equivalent to about a 50% protein feline pet food.

3 Claims, No Drawings

SENIOR FELINE FOOD

BACKGROUND OF INVENTION

This invention relates generally to pet foods and more particularly to senior pet foods.

Senior pets are typically well attended to so that the senior pet generally has a high quality, palatable and nutritionally balanced food which typically includes protein in the diet normally above about 26% by weight. Fortunately the advances of veterinary medicine and good nutrition benefits are available to senior pets so that such pets live longer. However, due to the normal biological aging processes, over time such pets continue to age, and lose an unacceptable portion of vital lean body mass. Such loss of lean body mass results in premature depletion of muscle and internal organs and can be irreversible. Older pets such as senior cats are more susceptible to such depletion than are younger cats. This undesired depletion is aggravated when inadequate protein is consumed by the senior cat in its diet, such as for example when the protein level in the diet of a senior cat is reduced and more pronounced when the dietary protein level drops below about 26% by weight.

Lean body mass plays a pivotal role in the biochemistry of a cat. Lean body mass exists as a reservoir within the body of the cat for protein turnover (proteins are constantly being broken down and new proteins produced). Lean body mass thus provides amino acids for the cat's synthesis of its life critical proteins such as immunoglobulin, hemoglobin, hormones and enzymes. Lean body mass provides nitrogen reserves to expend and so if there is a reduction in lean body mass, the feline has less nitrogen reserves to expend. Lean body mass is required for growth and maintenance of body tissues, including muscle and bone.

Reduced dietary protein is associated with diminution and loss of feline immune function. The immune system is the principal first line defense against the invasion of antigens into the feline body. Diminution and loss of immune function subjects the cat to the possibility of being unable to successfully defend against a body invasion of antigens, bacteria and viruses. Excessive loss of lean body mass is associated with undesirable high feline morbidity and mortality.

SUMMARY OF INVENTION

In one aspect, a pet food is provided comprising a first dietary level of protein and a supplemental amount of at least one amino acid in an amount effective to maintain lean body mass protection equivalent to a pet food containing a second dietary level of protein which is higher than the first dietary level of protein.

In another aspect, a food is provided comprising a dietary protein level and a supplemental amount of at least one amino acid sufficient to maintain muscle mass in a senior feline.

In another aspect, a food supplement is provided comprising at least one amino acid in an amount effective to maintain feline lean body mass protection substantially equivalent to a pet food containing a first dietary protein level when the feline is fed a pet food containing a second, lower, dietary protein level in combination with the food supplement.

In another aspect, a process is provided for preparing a feline food which comprises providing as a part of a feline ration, a supplemental amount of at least one amino acid in an amount effective to provide a feline lean body mass protection equivalent to that attainable from a diet containing about 50% protein.

In another aspect, a method is provided for retarding premature aging of a feline. The method comprises incorporating, in a feline food having a protein content of less than about 35%, a supplemental amount of at least one amino acid in an amount effective to retard premature aging compared to premature aging experienced by a feline fed the food without the supplemental amount of the at least one amino acid. The method also comprises feeding the food with the supplemental amount of the at least one amino acid to the feline.

In another aspect, a method is provided for providing a feline with enhanced health benefits derived from its diet. The method comprises incorporating in a feline food a supplemental amount of at least one amino acid in an amount sufficient to provide enhanced health benefits over that accorded by the food without the supplemental amount of the at least one amino acid. The method also comprises feeding the food with the supplemental amount of the at least one amino acid to the feline.

In another aspect, a method is provided for maintaining senior feline immune function. The method comprises incorporating, in a feline diet having a dietary protein level less than about 35%, a supplemental amount of at least one amino acid selected from lysine and cysteine in an amount sufficient to maintain the senior feline immune function substantially equivalent to that attainable from a diet containing about 50% protein. The method also comprises feeding the diet with the supplemental amount of the at least one amino acid to the feline.

In another aspect, a method of compensating for a lowered dietary protein level in a feline diet is provided. The method comprising feeding a feline an amount of at least one amino acid sufficient to compensate for the lowered dietary protein level by providing substantially the same lean body mass protection to the feline that a feline diet including a higher dietary protein level would provide.

DETAILED DESCRIPTION

Exemplary embodiments of pet foods and methods of manufacturing the pet foods are described below. In one embodiment, the pet is a senior feline and the pet food is a feline food including a supplemental amount of at least one amino acid in an amount sufficient to compensate for a low protein level in the pet's diet. In one embodiment, the amino acid is selected from lysine and/or cysteine. In addition, the supplemental amount of the amino acid maintains immune function and lean body mass, provides the feline with enhanced health benefits, retards pre-mature aging, and maintains muscle mass of a senior feline. Although exemplary embodiments are described herein, the pet food and methods are not limited to those specific embodiments. In particular, although extruded pet food is described in detail, it should be understood that the below described invention is applicable to canned foods as well as baked dry foods.

As used herein, the term senior feline refers to a feline which is generally about seven (7) years old or older and includes cats characterized as mature, or geriatric. Whether a cat is geriatric depends to some degree upon the activity level exhibited by the cat as well as its chronological age. Typically a geriatric cat is a senior cat exhibiting low physical activity level. Further, as used herein the term feline includes cats scientifically classified as *Felis catus*.

As used herein, the term feline food includes dry feline food, semi-moist feline food, intermediate moist and canned feline foods. Various sizes and shapes of food may be employed as long as the food is acceptably consumable by the feline in an amount so that the feline receives a normal daily ration providing the known essential nutrients. The method of delivery of food to the feline includes an effective method of delivery so that the supplemental amino acid is made available to the feline's gastro-intestinal tract and is digestible. Encapsulated lysine and/or cysteine may be employed. If desired, feeding may be carried out by feeding the feline one or more times per day.

As used herein, the term effective amount includes an amount which enables a cat consuming a supplemental amount of amino acid to have an effective lean body mass protection equivalent to or substantially equivalent to the lean body mass protection provided to a cat that consumes a 50% protein feline food diet or ration. It is understood that the cat's biochemical system produces the enhanced effective lean body mass protection in situ from digestion of the supplemental amino acid, e.g., lysine, cysteine and mixture of lysine and cysteine, so that there is an enhanced and bolstered lean body mass protection As used herein, the term feeding includes providing to the feline as a feline consumable form for uptake in the feline gastrointestinal tract. As used herein, the term feeding includes feeding with, feeding as a part of, feeding at the same or nearly same time, feeding at different times as well as feeding in a sequence of events whereby the diet and supplement are provided to the feline for oral ingestion and digestion.

In one embodiment, an extrusion method of incorporating an amino acid in a feline food product is provided which includes adding supplemental amino acid(s) to a pet food meal pre-mix, extruding the premix to form a feline food product, reducing the pet food to an appropriate cat consumable size, and drying the pet food product. In an exemplary embodiment, the supplemental amino acids include at least one of lysine and cysteine. In another embodiment, a method is provided which includes coating a dried, reduced to size pet food product with supplemental amino acid(s) in an amount sufficient to provide the desired enhanced lean body mass protection. The amino acids may be, for example, lysine and/or cysteine. In a further embodiment, the method includes adding supplemental amino acids to the meal premix and as a coating to the extruded, dried product.

In preparing an extruded dry pet food, nutritionally acceptable pet food ingredients (including protein, carbohydrates, and fats along with any appropriate binders, excipients, dispersants, etc.) are admixed and blended in a mixer or a series of mixers to form an extruder pre-mix. The mixing can be carried out in any manner which is effective to provide a sufficiently homogenous blend to permit further processing. Suitable mixers include any mixer having effective mixing capability and include illustratively Hobart single and double shaft mixers from Hobart Corporation, 701 South Ridge Avenue, Troy, Ohio, 45374.

After mixing the macro and micro ingredients comprising a protein source, a carbohydrate source, fat, ash, fiber and water, the extruder pre-mix is subjected to an extruder. In one embodiment, the supplemental amino acids are added to the extruder at this time. The temperature and moisture content of the mixture is adjusted to predetermined levels, for example, a temperature in the range from about 190° F. to about 220° F. and a moisture content in the range from about 20% to about 35% by weight moisture content, prior to adding the mixture to an extruder.

The extruder employed in the described process may be any convenient mechanical extruder type device which has the capability to input sufficient mechanical (and electrical energy) to an extruder mix and provide a masticated well mixed extrudate product which normally exits the extruder through a distal dieface. Illustratively useful extruders include Baker Perkins extruders manufactured by B & P Process Equipment and Systems, LLC, 1000 Hess Avenue, Saginaw, Mich., 48601.

Extrusion is performed at a moisture content of about 35%. The extrusion process exposes proteins in the extruder pre-mix to high temperatures (150°-200° C.) high pressures (17-60 atmospheres) and mechanical shear to convert the extruder pre-mix to a continuous plastic melt. During residence in the extruder, the ingredients are also cooked. When the melt is forced from the die, the pressure drops suddenly to atmospheric pressure, with a resulting release of steam held within the extrudate, resulting in expansion and porosity of the extrudate.

The melt is extruded through an extruder diecap or die face having a plurality of openings. The extruded product is cut or severed to a size of about 0.1 inch to about 0.5 inch to form pieces or kibbles. In one embodiment, a severing or cutting blade is positioned a short distance from the dieface to cut the extrudate. After the kibbles exit the extruder, they are dried in a suitable dryer at a temperature from about 290° F. to about 340° F. and a moisture content of, for example, from about 5% to about 15%. The kibbles are optionally coated or dusted with a suitable coating material. The coating material can be, for example, liquid animal digest, concentrated liquid animal digest, animal or poultry fat, or a dry coating such as dried yeast and may include the supplemental amino acids. The finished pet food product is packaged for sale and ultimately fed to pets such as cats.

As described above, a method is provided which includes incorporating at least one supplemental amino acid into the extruded food product and/or coating the food product with the at least one supplemental amino acid. The feline consumes the food containing the at least one supplemental amino acid and after ingestion, the supplemental amino acid is made available to the feline's gastrointestinal tract and for subsequent insynthesis of proteins such as immunoglobin, hemoglobin, hormones and enzymes.

Illustrative nonlimiting examples of proteins typically included in a feline diet are those derived from meats consumed by a carnivore, including lamb, beef, chicken, deer, turkey, pork, buffalo, bison and ostrich. Additional protein sources include proteins from vegetable matters, such as soybeans, corn gluten and others, and from dairy products such as whey and casein. It is understood that the feline is adequately supplied with critical amino acids such as L-taurine, methionine and L in its ration.

Lysine and cysteine may be purchased commercially (Ajinomoto Heartland, 8430 West Bryn Mawr, Suite 650, Chicago, Ill. 60631) or may be prepared from any suitable source. One useful lysine is Liquid Lysine 60. Pure crystalline amino acids are readily available commercially and may be used since they have a high digestibility and high absorption by the gastrointestinal system of a feline. A preferred cysteine is L-cysteine (Source is Ajinomoto, supra). Useful lysine and cysteine and materials containing them may be purchased from Sigma Aldrich, St. MO, USA. (see http:\\www.sigmaaldrich.com).

As used herein, the terms lysine and cysteine include the free acid, analogs and/or water soluble salt forms respectively of amino acids lysine and cysteine. Illustrative non-limiting useful forms of lysine and cysteine include the free acids lysine as L-lysine, or D-lysine; cysteine as L-cysteine, the monohydrochloride (HCl) salt and hydrate and anhydrous forms.

Other sources of lysine and cysteine include di-amin compounds e.g. L-lysince-L-glutamate and L-lysine-L-glutamate and L-lysince-L-asparate forms and acetylated forms e.g.

N-acetyl-cysteine; L-cysteine hydrochloride anhydrous, L-cysteine hydrochloride monohydrate, L-cysteine, L-cysteine dihydrochloride, L-cystine, L-lysine free base and L-lysine monohydrochloride.

Useful lysines include those from poly-amino acids consisting in whole or in part of lysine including Poly-D-lysine hydrobromide, molecular weight about 70,000 to about 150,000; Poly-L-lysine hydrochloride, molecular weight about 15,000 to about 30,000; Poly-L-lysine hydrobromide, molecular weight about 150,000 to about 300,000; and Poly (Lys, Phe) 1:1 hydrobromide, molecular weight about 20,000 to about 50,000 daltons.

Useful lysines and cysteines also include those from peptide combinations, provided that these are feline digestible, such as 1-, 2-, 3-, etc. amino acids in length, presumably enhanced for lysine and/or cysteine (e.g. cys-lys-x, poly-cys, poly-lys, etc.) The amounts of lysine and cysteine employed in the diet or ration to the gastro-intestinal system of the feline will vary depending on a number of factors including type of cat, age of cat, cat food used, protein level in the diet, degree of lean body mass protection desired, and other factors.

In one embodiment, cysteine levels in the range from about 0.50% to about 0.75% of the feline diet are fed to a senior cat. More particularly, cysteine levels in the range from about 0.60% to about 0.66% of the feline diet are fed to a senior cat to provide the beneficial lean body mass protection to the cat. Further, cysteine levels in the range from about 1.67% to about 2.68% of the dietary protein level of the feline diet are fed to a senior cat. In addition, cysteine levels in the range from about 2.0% to about 2.4% of the dietary protein level of the feline diet are fed to a senior cat to provide beneficial lean body mass protection.

Additionally, or in the alternative, lysine levels in the range from about 2.0% to about 3.5% of the feline diet are fed to a senior cat. More particularly, lysine levels in the range from about 2.7% to about 3.1% of the feline diet are fed to a senior cat to provide the beneficial lean body mass protection to the cat. Further, lysine levels in the range from about 6.7% to about 12.5% of the dietary protein level in the feline diet are fed to a senior cat. In addition, lysine levels in the range from about 9.0% to about 11.0% of the dietary protein level of the feline diet are fed to a senior cat to provide beneficial lean body mass protection.

In one embodiment, lysine and/or cysteine are intimately mixed with the feline food. In an alternative embodiment, lysine and/or cysteine are applied to the food by spraying them onto the exterior of the feline food in an adherent fashion. As a further example, lysine and/or cysteine are individually prepared and provided to the cat as a supplemental food, mix, or dissolved in water whereby the cat drinks the supplement in its water.

In one embodiment, the amino acid(s) are diluted prior to incorporating the amino acid(s) with the feline food. The diluent is one of a solid and a liquid, is compatible with the amino acid(s) and feline food, and is palatable, non-adverse, and gastro-intestinally acceptable to, and safe for eating by, the feline. The amino acid(s) may be admixed with the feline food by normal mixing of amino acids with the feline food. Further, an auxiliary component may be added to a feline food which has the supplemental amino acid(s) incorporated therein or therewith. This addition may be accomplished by applying the auxiliary components as a coating to the food product.

Lean body mass of a feline is determined by determining body composition analysis (BCA). Useful BCA analysis measurement methods include measuring fat-free total body electrical conductivity (TOBEC), BOD POD (air displacement), BIA (bioelectrical impedance, hydrodensitometry weighing (underwater)), quantitative computed tomography (QCT), NIR (near infrared interactance), MRI (magnetic resonance imaging), isotopic dilution techniques and dual energy X-ray absorptionmetery (DEXA).

A DEXA analysis is a BCA used to determine the lean body mass protection provided by a ration consumed by a feline. The most commonly used techniques for determining lean body mass are single- and dual-energy X-ray densiometry (SXA or DEXA). Typically a DEXA analysis is done by scanning a whole body using two different sources of wave lengths of low dose x-rays which are targeted at a density measurement subject. The amount of lean body mass is calculated based on differential refraction of the two different wavelengths.

In an isotopic dilution technique, a count is taken of radioactive potassium 40 for a feline body and a total potassium content is estimated for the feline. Since it is known that potassium is the principal ion in cells of active feline lean tissue mass, one can estimate the amount of lean body mass present in the feline.

In another embodiment, tritiated or deuterated water, or a chemical tracer such as antipyrine is used to provide an estimate of feline total body water since it is known that fats of felines hold little water.

It has been determined that cats consuming a food containing a dietary protein level of about 28-35% will have corresponding lower lean body mass than cats which have been consuming a food containing a dietary protein level of at least about 50% or higher. For cats having a lean body mass below that associated with a comparatively aged cat fed 50% or more protein, supplemental amino acids are added to the food or a food supplement is used. When cats are fed the supplemental amino acids as explained above, lean body mass is maintained at a level corresponding to that of a cat fed a diet containing a 50% dietary protein level. Thus the cat has been provided with an increased lean body mass protection and it is believed that use of supplemental amino acids retards the onset of decreased lean body mass protection. In an exemplary embodiment, lysine and/or cysteine are used as the amino acids.

While the invention has been described in terms of various specific embodiments, those skilled in the art will recognize that the invention can be practiced with modification within the spirit and scope of the claims.

The invention claimed is:

1. A pet food comprising a mixture of a protein, a carbohydrate, a fat, a first dietary level of protein and supplemental amounts of lysine and cysteine in amounts effective to maintain lean body mass protection in a senior feline equivalent to a pet food containing a second dietary level of protein which is higher than the first dietary level of protein, the lysine comprising from about 2.7% to about 3.1% by weight of the pet food and the cysteine comprising from about 0.50% to about 0.75% by weight of the pet food, wherein the pet food is at least one of an extruded food, a canned food, and a baked dry food.

2. A pet food comprising a mixture of a protein, a carbohydrate, a fat, a dietary protein level and supplemental amounts of lysine and cysteine in amounts sufficient to maintain muscle mass in a senior feline, the lysine comprising from about 6.7% to about 12.5% by weight of the dietary protein level of the pet food and the cysteine comprising from about 1.67% to about 2.68% by weight of the dietary protein level of the pet food, the dietary protein level comprising from about 28% to about 35% by weight of the pet food dry matter.

3. A pet food comprising a mixture of a protein, a carbohydrate, a fat, a dietary protein level and supplemental amounts of lysine and cystein in amounts sufficient to maintain muscle mass in a senior feline, the lysine comprising from about 6.7% to about 12.5% by weight of the dietary protein level of the pet food and the cysteine comprising from about 1.67% to about 2.68% by weight of the dietary protein level of the pet food, the dietary protein level comprising from about 28% to about 35% by weight of the pet food dry matter, wherein the amount of the at least one amino acid is sufficient to maintain the muscle mass of a senior feline substantially equivalent to that attainable from a pet food including a 50% by weight dietary protein level.

\* \* \* \* \*